United States Patent [19]

Moss

[11] 3,948,900

[45] Apr. 6, 1976

[54] PREPARATION OF 1-METHYLPIPERAZINE AND 1,4-DIMETHYLPIPERAZINE AS CO-PRODUCTS

[75] Inventor: Philip Hotchkiss Moss, Austin, Tex.

[73] Assignee: Jefferson Chemical Company, Inc., Houston, Tex.

[22] Filed: Aug. 16, 1974

[21] Appl. No.: 498,188

[52] U.S. Cl. ......................................... 260/268 SY
[51] Int. Cl.² ..................................... C07D 295/04
[58] Field of Search ............................. 260/268 SY

[56] References Cited
UNITED STATES PATENTS 3,249,613   3/1966   Burns et al. .................... 260/268 SY Primary Examiner—Richard J. Gallagher
Assistant Examiner—Jose Tovar
Attorney, Agent, or Firm—James L. Bailey; John R. Kirk, Jr.; Lee G. Meyer

[57] ABSTRACT

A process for the preparation of 1-methylpiperazine and 1,4-dimethylpiperazine as co-products is disclosed which provides a crude reaction product free of piperazine impurity. The process of the invention comprises mixing and reacting formaldehyde and piperazine at a molar ratio of more than 1.3 to less than about 2.0 and then hydrogenating the resulting reaction product carried in methanol as a major solvent in liquid phase at a temperature of about 60°–130°C. in the presence of a nickel or cobalt hydrogenation catalyst. The crude hydrogenated reaction product is free from piperazine impurity from which 1-methylpiperazine and 1,4-dimethylpiperazine can be readily separated in substantially pure form such as by simple fractional distillation.

9 Claims, No Drawings

PREPARATION OF 1-METHYLPIPERAZINE AND 1,4-DIMETHYLPIPERAZINE AS CO-PRODUCTS

BACKGROUND OF THE INVENTION

1. Field of the Invention.

This invention relates to the preparation of piperazine derivatives and more particularly pertains to an improved process for preparing 1-methylpiperazine and 1,4-dimethylpiperazine as co-products free from piperazine impurity. 1-methylpiperazine and 1,4-dimethylpiperazine have utility as curing agents for resins, as intermediates for drugs, and in the synthesis of dyes and derivatives having pharmacological utility.

2. Description of the Prior Art.

Processes for the preparation of 1-methylpiperazine and 1,4-dimethylpiperazine by the catalytic hydrogenation of the reaction product of formaldehyde and piperazine are well-known in the art. Generally, such procedures include mixing and reacting formaldehyde and piperazine in an aqueous medium at a molar ratio between 1:1 to 2:1 formaldehyde:piperazine and then hydrogenating the crude reaction product carried in a liquid solvent in the presence of a hydrogenation catalyst under mild hydrogenation conditions. 1-methylpiperazine and 1,4-dimethylpiperazine can be separated in good yields from the hydrogenated crude reaction product. Baltzly et al (Journal American Chemical Society, 66 (1944), pp. 63–66) and Prelog and Stepan (Coll.Trav.Chim.Tchecosl. 7, (1935), pp. 93–102) disclose procedures for the preparation of the above-mentioned mono- and di-alkylated piperazines. More particularly, U.S. Pat. No. 2,639,284 to Morren, discloses the preparation of 1-methylpiperazine by the process of mixing and reacting piperazine hexahydrate and 34.5% aqueous formaldehyde, in a piperazine:formaldehyde molar ratio of 1:1 in butanol or ethanol solvent and then catalytically hydrogenating the reaction mixture under mild conditions resulting in a product high in 1-methylpiperazine which also contains substantial amounts of 1,4-dimethylpiperazine and piperazine. W. T. Forsee, Jr. and C. B. Pollard, J.Am.-Chem. Soc. 57, 1788 (1935), describe the formation of an 88% yield of 1,4-dimethylpiperazine from the reaction of piperazine and aqueous formaldehyde (1:2 molar ratio of piperazine:formaldehyde) with subsequent treatment with hydrogen generated by zinc and hydrochloric acid. German Pat. No. 1,932,422 (1971) discloses admixing formaldehyde, water, piperazine and isobutanol as solvent and then hydrogenating the reaction mixture to provide 90.5% methylpiperazine upon distillation of the hydrogenated product. French Pat. No. 1,592,964 describes a process whereby an aqueous solution of piperazine (60 wt.% piperazine) and 30% aqueous formaldehyde are mixed and reacted in the presence of piperazine acetate with subsequent hydrogenation of the reaction mixture to provide a reaction product containing 99.3% methylpiperazine and piperazine.

Although 1-methylpiperazine and/or 1,4-dimethylpiperazine can be produced in high yields by any of the aforementioned processes by adjusting the molar ratio of piperazine:formaldehyde, these known processes have suffered from the disadvantage of producing crude hydrogenated reaction products containing piperazine as an impurity, either as unreacted product or as a by-product. The separation of substantially pure 1-methylpiperazine from such crude reaction products containing piperazine has been found to be most difficult, if not impossible, as a practical matter. The presence of piperazine as an impurity in 1-methylpiperazine limits the utility of 1-methylpiperazine, particularly in the pharmacological industry for the preparation of certain drugs. Piperazine is also reactive and can form other undesirable derivative impurities. In fact, 1-methylpiperazine containing as little as 0.1 wt.% piperazine cannot be employed in the manufacture of many drug derivatives for human and/or animal use.

Even recognizing the difficulties in separating essentially pure 1-methylpiperazine and/or 1,4-dimethylpiperazine from admixture with piperazine, it has heretofore been the common practice in the industry to prepare such products by the above-mentioned processes employing formaldehyde and piperazine feeds in conjunction with extensive separation techniques. For example, U.S. Pat. No. 2,639,284 teaches the addition of carbon disulfide to the hydrogenated formaldehyde-piperazine reaction product mixture and subsequent treatment with concentrated hydrochloric acid with reflux for the preparation of the desired 1-methylpiperazine. U.S. Pat. No. 2,919,275 discloses the separation of 1-methylpiperazine by selective precipitation of the diacetate derivative from which the 1-methylpiperazine can be regenerated through caustic hydrolysis. U.S. Pat. No. 3,069,331 teaches a process for the separation of piperazine and 1-methylpiperazine by extensive extractive distillation of the mixture in the presence of a countercurrent flow of ethylene glycol.

Although some of the aforementioned procedures have apparently been successful to some extent in the preparation of substantially pure 1-methylpiperazine and/or 1,4-dimethylpiperazine products, they all involve extensive reaction procedures and/or extensive treatment of the hydrogenated crude reaction products which inherently adversely affect the economics of the preparation of the desired product.

Surprisingly, I have now found that 1-methylpiperazine and 1,4-dimethylpiperazine can be prepared from formaldehyde and piperazine as co-products in a crude reaction product mixture which contains no free piperazine as an impurity. It is believed that my invention is a tremendous advance in the art of preparing such products in essentially pure form. Most unexpectedly, I have discovered that the molar ratio of piperazine:formaldehyde employed, the particular liquid solvent employed, and the particular amount of water present during the hydrogenation of the crude reaction product of piperazine and formaldehyde affect the presence of piperazine in the crude hydrogenated reaction product. Through the practice of my invention, 1-methylpiperazine and/or 1,4-dimethylpiperazine can be produced in essentially pure form without the requirement of subjecting the product to the aforementioned extensive procedures for separating piperazine impurity. Essentially pure 1-methylpiperazine and 1,4-dimethylpiperazine products can be obtained in the practice of my invention by relatively simple, well-known distillation techniques.

SUMMARY OF THE INVENTION

The present invention is an improvement of the process for preparing 1-methylpiperazine and 1,4-dimethylpiperazine as co-products by the catalytic hydrogenation of the reaction product of formaldehyde and piperazine. The improvement takes place in the reaction and comprises mixing and reacting formaldehyde and piperazine at a molar ratio of from more than 1.3:1 to less than about 2.0:1 and hydrogenating the resulting reaction product employing methanol as the major solvent in the presence of less than about 35% by weight water, based upon the weight of total solvent present. The hydrogenation is carried out in the liquid phase by heating the reaction product, diluted in methanol, in the presence of a hydrogenation catalyst at a temperature of between about 60°C. to about 130°C. Surprisingly, mixing and reacting formaldehyde and piperazine at the above molar ratios, and hydrogentating the reaction product employing methanol as the major solvent in the presence of no more than about 35 wt.% of water, based on total solvent present, provides a resulting crude hydrogenated product containing no piperazine impurity, as by-product or unreacted product, and 1-methylpiperazine and/or 1,4-dimethylpiperazine can be separated therefrom in essentially pure form by relatively simple distillation or any other conventional separation technique.

DETAILED DESCRIPTION OF THE INVENTION

In accordance with the present invention, formaldehyde and piperazine are mixed together at a molar ratio between the range of more than 1.3:1 to less than about 2.0:1, and preferably between about 1.4:1 to about 1.7:1 moles formaldehyde:moles piperazine. The admixture results in an exothermic reaction and is maintained at a temperature between about 35°–65°C. by cooling until the reaction is complete which usually occurs within the range of about 0.5 to about 2 hours. The particular time necessary for carrying and a given reaction is dependent upon the rate at which the generated heat is removed. The formaldehyde can be employed as paraformaldehyde or as aqueous formalin, e.g. about 30–40% aqueous formalin. Moreover, the piperazine may be employed in the form of anhydrous piperazine or piperazine hexahydrate, forms in which piperazine is usually marketed commercially. However, as more particularly described hereafter, caution must be taken when aqueous forms of the reaction components are utilized so as to minimize the amount of water present during subsequent hydrogenation in order to accomplish the desired objectives of producing a crude hydrogenated reaction product containing no free piperazine. Otherwise, at least some water must be removed from the reaction product mixture prior to hydrogenation to provide an amount below the maximum allowable as described more particularly hereafter.

The reaction of piperazine and formaldehyde inherently produces water. Moreover, for economic reasons, it is preferred to employ formaldehyde in the form of an aqueous solution, i.e. formalin, in concentrations within the range of about 30–40% by weight formaldehyde. Nevertheless, even employing aqueous formalin in such concentrations with the amount of water inherently produced, the resulting reaction product is highly concentrated. Therefore, it is preferred to carry out the formaldehyde:piperazine reaction in the presence of sufficient liquid solvent to bring the formaldehyde:piperazine reaction product to a viscosity low enough to permit stirring.

The choice of liquid solvent is not critical during the formaldehyde:piperazine reaction and can be water, or a lower alcohol such as methanol, ethanol, propanol, or butanol. However, I prefer to employ methanol. If ethanol, propanol, or other lower alcohols are employed, they must be removed and replaced by methanol prior to subsequent hydrogenation in order to accomplish the desired objectives of the invention. Utilizing one solvent for the reaction step and then changing to methanol for sufficient hydrogenation would not be practicable. Moreover, a loss of formaldehyde would occur during any such solvent replacement for free formaldehyde would be in equilibrium with the methylolated piperazine in the reaction product mixture. The employment of water as the sole solvent may require adjustment of the water content so as to provide no more than 35 wt.% water, based upon the weight of solvent present, in the reaction product mixture during subsequent hydrogenation.

The specific amount of methanol which can be added as a solvent for a given reaction of formaldehyde and piperazine to bring the reaction product to a viscosity low enough to permit stirring can be readily determined by one having ordinary skill in the art without undue experimentation. By way of example, experiments have shown that mixing and reacting the formaldehyde and piperazine at lower molar ratios within the above-described range requires increasingly more methanol solvent. In addition, where aqueous forms of the reactants are employed, less methanol solvent is required.

As known, formaldehyde and piperazine react in a 2:1 formaldehyde:piperazine molar ratio to form 1,4-bis(hydroxymethyl)piperazine which, when hydrogenated, is converted to 1,4-dimethylpiperazine in high yields. It is also known that mixing and reacting formaldehyde and piperazine in a 1:1 molar ratio results in the formation of a white, insoluble high-melting precipitate which has been found to be poly(methylenepiperazine). Hydrogenation of this white polymer provides a crude reaction product containing 1-methylpiperazine plus smaller amounts of 1,4-dimethylpiperazine and piperazine. The reaction of formaldehyde and piperazine in ratios between 2:1 and 1:1 formaldehyde:piperazine yields mixtures of dimethylolated piperazine and the white polymer poly(methylenepiperazine). Heretofore, hydrogenation of such reaction products in accordance with conventional hydrogenation procedures in the presence of conventional hydrogenation catalysts have resulted in crude products containing 1-methylpiperazine and 1,4-dimethylpiperazine along with piperazine, the amount of undesirable piperazine being present in increasing amounts as lower molar ratios are employed. This would be expected theoretically since piperazine would result from hydrogenation of the polymer poly(methylenepiperazine). However, most surprisingly, it has been found that the employment of formaldehyde:piperazine molar ratios of about 1.3:1 to below 2.0:1, especially to below 1.7:1, in the formaldehyde-piperazine reaction with subsequent hydrogenation in accordance with the present invention results in the formation of a crude reaction product entirely free of piperazine. Hence, the present invention is specifically directed to the employment of formaldehyde:piperazine molar ratios within this range. These ratios make available a wide range of methylpiperazine:1,4-dimethylpiperazine co-product weight ratios of from above about 60:40 to about 0:100, theoretically, essentially free of piperazine according to the reactant chosen.

Another critical feature of the present invention is the employment of methanol as the major carrier solvent during subsequent hydrogenation of the formaldehyde-piperazine reaction product. As illustrated in the examples set forth hereafter, it has been found that the utilization of other solvents as the major solvent, such as water, ethanol, isopropanol, and the like under the same hydrogenation conditions in the same formaldehyde:piperazine molar ratios, result in crude hydrogenated reaction products containing piperazine as an impurity. "Major amount of methanol" or "major solvent", as used herein, is meant to include an amount by weight in excess of any other solvent carrier of the reaction product which may be present. Preferably, methanol is employed in an amount sufficient to provide a concentration of the formaldehyde-piperazine reaction products of about 15–30%, based upon the total weight of solvent and reaction product present, during hydrogenation. The specific amount of methanol required to provide such a concentration is dependent upon the amount of water present which can be from the employment of aqueous solutions of reactants and from the reaction itself. As mentioned hereinbefore, it is preferred to add methanol as a solvent to the formaldehyde and piperazine prior to or during the reaction between these compounds. This eliminates the subsequent requirement of methanol solvent addition prior to hydrogenation of the formaldehyde-piperazine reaction product.

Still another critical factor of the invention, as more particularly described and shown in the examples set forth hereafter, is that large amounts of water present during hydrogenation of the formaldehyde:piperazine reaction product can adversely affect the desired results. It appears that it is not possible to carry out the process of the invention in an anhydrous medium inasmuch as water is formed in the process. Moreover, the employment of paraformaldehyde and anhydrous piperazine is not preferred because of slower hydrogenations which affect the economics of the inventive process. Yet, the presence of some water during hydrogenation does not affect the desired results of providing a crude hydrogenated product mixture with no piperazine impurity, provided the water is present in an amount of no more than about 35% based upon the weight of total solvent present with the reaction product to be hydrogenated. Preferably, no more than 30 weight % water is present in the solvent carrier as the reaction product slurry is subjected to the hydrogenation step.

The amount of water present during hydrogenation can be effectively controlled by the concentration of formaldehyde and piperazine employed as aqueous solutions and the amount of methanol solvent employed. As mentioned hereinbefore, the process of the invention is preferably carried out by employing an aqueous solution of formaldehyde, i.e. formalin, containing at least about 30 wt.% formaldehyde. Moreover, commercially available piperazine is preferably employed which is usually anhydrous, but may be piperazine hexahydrate or a piperazine-water eutectic containing 56.4% piperazine and 43.6% water by weight. Thus, by careful control of the reactants in aqueous solution, along with the employment of the preferred amounts of methanol solvent set forth hereinabove, the amount of water present in the solvent during hydrogenation can be readily controlled so that no more than 35%, based upon the total weight of solvent, is present.

The formaldehyde-piperazine reaction product, carried in methanol as the major solvent along with no more than the above-described amount of water present, is then hydrogenated by heating in the presence of hydrogen and a hydrogenation catalyst, such as a nickel and/or cobalt-containing catalyst, at a temperature within the range of about 60° to about 130°C. under a pressure sufficient to maintain the medium in liquid phase which is usually within the range of from about atmospheric to 4,000 psig. Preferably, temperatures within the range of about 70° to about 120°C. and a pressure of between about 50 to about 150 psig are employed. Higher temperatures and pressures can be employed, but have not been found to provide any improved results to justify the expensive equipment required and increased operating costs. The heating is continued in the presence of the hydrogenation catalyst until hydrogen is no longer consumed, indicating complete hydrogenation.

Any conventional hydrogenation catalyst can be employed, particularly those containing nickel or cobalt. Furthermore, the catalysts can be employed as unsupported or supported on conventional carriers inert to the hydrogenation conditions which are well-known in the art. These catalysts are well-known in the art and will not be specifically discussed.

The particular amount of catalyst employed during the hydrogenation is not critical and merely affects the rate of hydrogenation. We prefer to employ about 5 to about 15 wt.% of active metal catalyst, based on the piperazine charged. However, as little as 1–5% would be operable, with quantities above about 10–15% providing no additional advantage.

The resulting crude hydrogenated reaction product, prepared in accordance with the process described hereinabove, has been found, upon analysis, to contain 1-methylpiperazine and 1,4-dimethylpiperazine as co-products with no detectable free piperazine being present. 1-methylpiperazine and 1,4-dimethylpiperazine can be readily separated from the crude product in essentially pure form by conventional simple distillation techniques, such as fractional distillation and the like.

The critical features and the advantages of the invention will become further apparent from the following examples which illustrate the best mode contemplated for carrying out the invention.

EXAMPLE I

In a reaction vessel equipped with stirring means and cooling means, a solution of 860 g. (10.0 moles) of piperazine in 1.5 gallons of methanol was added to 1115 g. (13.7 moles) of 37% formalin with stirring and sufficient cooling to keep the temperature of the reaction mixture below 45°C. The resulting reaction product, a slurry of poly(methylenepiperazine) in a methanol-water solution of bis(hydroxymethyl)piperazine containing 14 wt.% water in the solvent, was then charged to a 3-gallon autoclave together with 35 g. of pre-reduced nickel-on-kieselguhr hydrogenation catalyst. The autoclave reaction vessel was sealed, purged of air and pressurized by the introduction of hydrogen. Hydrogenation was conducted at a temperature of 86°–90°C. at 50 psig hydrogen pressure maintained by intermittent hydrogen introduction into the vessel until no further consumption of hydrogen was evident, a period of 6 hours. The hydrogenated crude reaction product was then removed from the autoclave vessel and analyzed by gas liquid chromatography. Analysis of the unrefined product, adjusting results to exclude methanol and water, showed it contained 58.0% 1- methylpiperazine, 41.7% 1,4-dimethylpiperazine, 0.3% N,N-dimethylaminoethanol (arising from monoethanolamine impurity in the piperazine), and no piperazine.

EXAMPLE II

Employing the reaction equipment described in Example I, 840 g. (10.3 moles) of 37% aqueous formaldehyde was added to a solution of 860 g. (10.0 moles) of piperazine in 1.5 gallons of methanol. The admixture was maintained at a temperature of 30°–50°C. during formaldehyde addition with cooling. The resultant reaction mixture, primarily a slurry of poly(methylenepiperazine) and containing 12 wt.% water in the solvent, was then charged into an autoclave containing Raney nickel and hydrogenated under 100 psig of hydrogen at 75°–85°C. in accordance with the procedure described in Example I until hydrogenation was complete, as indicated by a cessation of hydrogen consumption which occurred after about 10 hours. Analysis of the resultant product solution by gas liquid chromatography on a water-methanol free basis showed the product contained 75.0% 1-methylpiperazine, 16.3% 1,4-dimethylpiperazine, and 8.6% piperazine, by weight. A comparison of these results to those of Example I illustrate the criticality of the formaldehyde:piperazine molar ratio upon the resultant crude hydrogenated product.

EXAMPLE III

In an appropriate reaction vessel, 744 g. of piperazine dissolved in 3,000 ml. of methanol was added to 850 g. of 37% formalin, with stirring. The temperature during addition was maintained with cooling at 35°–45°C. The formaldehyde-piperazine molar ratio was 1.22:1. The resultant slurry contained 21% by weight water in the solvent and was charged to a 3-gallon autoclave together with 125 g. of powdered, prereduced nickel-copper-chromia hydrogenation catalyst. The autoclave was sealed and purged of air by injection of hydrogen. Hydrogenation of the slurry was carried out at 50 psig pressure at 85°C. with intermittent hydrogen injection to maintain the pressure for 6 hours. Analysis of the hydrogenated product by gas liquid chromatography showed the composition to be 72.3% 1-methylpiperazine, 26.7% 1,4-dimethylpiperazine, and 0.7% piperazine, by weight (solvent free). After removal from the autoclave, the crude hydrogenated product was filtered to remove the catalyst and then distilled through a two-foot column containing a stainless steel packing. After removal of the methanol overhead, 1,4-dimethylpiperazine-water azeotrope was next collected, with addition of water to the distillation pot until the distillate was free of amine, indicating complete recovery of the 1,4-dimethylpiperazine. Distillation was continued at a 10/1 reflux ratio with the remaining water in the product being taken overhead, followed by 484 g. of 1-methylpiperazine, b.p. 137°–8°C. Analysis of the 1-methylpiperazine by gas liquid chromatography showed that it was 99% pure, but contained 0.55% piperazine, by weight. The results of this example, compared to those of Example I, also illustrate the effect of formaldehyde:piperazine molar ratio upon the preparation of a crude hydrogenated reaction product containing piperazine impurities. The example further shows the difficulty of separating 1-methylpiperazine in pure form, free of piperazine by a conventional distillation technique.

EXAMPLE IV

To a 15-gallon stainless steel kettle was charged 13.03 lbs. (72.9 gram moles) of 37% formalin. A solution of 9.89 lbs. (52.2 gram moles) of piperazine in 39.56 lbs. of methanol was introduced thereto over a period of one hour with cooling to maintain the temperature of the admixture between 35°–40°C. The mole ratio of formaldehyde:piperazine was 1.387:1 and the amount of water present after reaction was 9.85 lbs. (19%, by weight, concentration in the solvent). In all examples, the water calculated is that added with components, plus water formed when formaldehyde, piperazine go to poly(methylenepiperazine). Water produced during hydrogenation is not included. A hydrogenation catalyst, a powdered nickel on kieselguhr product (Harshaw Ni-1404, Harshaw Chemical Company), was also added to the kettle which was then sealed and pressurized to 50 psig by the introduction of hydrogen. The kettle was heated at 78°–94°C. while the admixture was stirred with intermittent hydrogen introduction to maintain the pressure at 50 psig until consumption of hydrogen was complete, a period of 4 hours. Gas liquid chromatography analysis of the unrefined hydrogenated product showed a composition, solvent-free, of 55.2% 1-methylpiperazine, 42.0% 1,4-dimethylpiperazine, and the remainder several minor unknowns, but no piperazine was detected. The hydrogenated product was then removed from the steel kettle, filtered and distilled in accordance with the procedure described in Example III, collecting methanol, 1.4-dimethylpiperazine-water azeotrope, water and finally 1-methylpiperazine product, b.p. 137°–8°C. Analysis of the 1-methylpiperazine product collected by GLC analysis showed it was of high purity and completely free of piperazine and 1,4-dimethylpiperazine. The results of this example illustrate that substantially pure 1-methylpiperazine product free of piperazine impurity can be obtained by a conventional simple distillation procedure of the hydrogenated product prepared in accordance with the process of the invention.

EXAMPLE V

A comparison of the results of this example with those of Example IV clearly show the adverse effect of employing water as the exclusive solvent during hydrogenation of the formaldehyde:piperazine reaction product. In an appropriate reaction vessel, a solution of 172 g. (2.0 moles) of piperazine in 622 g. of water was added to 227 g. (2.8 moles) of 37% formalin with stirring and cooling to maintain the temperature at 40°C. during admixture. The molar ratio of formaldehyde:piperazine was 1.4:1. The resulting white slurry containing only water as a solvent carrier was then admixed with 52 g. of a pre-reduced, powdered nickel hydrogenation catalyst in a 1-gallon autoclave. Upon sealing and purging of air with hydrogen, the autoclave was pressurized to 50 psig and heated to 95°C. Temperature and pressure were maintained with intermittent hydrogen injection until hydrogen consumption ceased, taking 4.5 hours. Analysis of the resulting hydrogenated product by gas liquid chromatography, solvent free, showed a composition including 39.2% 1-methylpiperazine, 47.7% 1,4-dimethylpiperazine, 6.2% piperazine and 6.7% of an unknown, higher boiling material.

EXAMPLE VI

To 672 g. (8.3 moles) of 37% formalin charged to an appropriate reaction vessel was added 510 g. (5.93 moles) of piperazine in 1818 g. of water with cooling to maintain the temperature at 30°C. The formaldehyde:-piperazine molar ratio was 1.4:1. The thick latex slurry was then mixed with 7.5% by weight, based on the total feed, of a powdered nickel hydrogenation catalyst in an autoclave and hydrogenated at 90°C. under 50 psig hydrogen partial pressure in 2.5 hours. Water was the sole solvent in this experiment. Analysis of the hydrogenated product by GLC, on a solvent-free basis, showed the product to be 41.9% 1-methylpiperazine, 48.2% 1,4-dimethylpiperazine, 7.4% piperazine, and 2.3% less volatile material. This example confirms the results obtained in Example V.

EXAMPLE VII

In accordance with the procedure described in Example VI, 70 g. (0.81 moles) of piperazine dissolved in 320 g. methanol was mixed with 85 g. (1.05 moles) of 37% formalin and maintained at 40°C. with cooling (formaldehyde:piperazine molar ratio of 1.3:1). The amount of water present in the reaction product slurry was 17 wt.% of the water-methanol solvent. The reaction product slurry was then hydrogenated as described in Example VI in the presence of a powdered nickel hydrogenation catalyst (Harshaw Ni-0104, Harshaw Chemical Company). Gas liquid chromatography analysis of the hydrogenated product, wt.% on a solvent-free basis, showed it contained 67.1% 1-methylpiperazine, 31.9% 1,4-dimethylpiperazine, and 0.2% piperazine. A comparison of the results of this example to those of Example VI illustrate the drastic improvement in the reduction of the amount of piperazine impurity present in the resulting hydrogenated product by controlling the amount of water present through the employment of methanol as the primary solvent during the hydrogenation step. This example also illustrates the criticality of employing a formaldehyde:piperazine molar ratio above 1.3:1 for the preparation of a crude reaction product entirely free of piperazine impurity, as compared to the results of Example IV.

EXAMPLE VIII

A solution of 86 g. (1.0 mole) of piperazine in 262 g. ethanol was added with stirring to 130 g. (1.6 moles) of 37% formalin in an appropriate vessel at a temperature of 30°-40°C. maintained with cooling. This slurry, containing 25 wt.% water and 75 wt.% ethanol as solvent, based on solvent weight, was then charged to an autoclave containing 14 g. of a supported nickel catalyst (Harshaw Ni-3266P, Harshaw Chemical Company) and stirred in a hydrogen atmosphere at 91°C. under 50 psig for 5 hours. Analysis of the crude product by gas liquid chromatography, calculating on a water-alcohol free basis, gave 60.4% 1,4-dimethylpiperazine, 38.2% 1-methylpiperazine, and 0.5% piperazine.

EXAMPLE IX

Example VIII was repeated except that 262 g. isopropanol was substituted for ethanol as the solvent. Hydrogenation was indicated to be complete in 4.5 hours. Analysis of the resultant hydrogenated product by gas liquid chromatography, calculated on a solvent-free basis, showed it contained 68.1% 1,4-dimethylpiperazine, 30.4% 1-methylpiperazine and 0.3% piperazine.

EXAMPLE X

A solution of 80 g. (0.94 mole) of piperazine in 320 g. of methanol was added to 105 g. (1.30 moles) of 37% formalin in a suitable reaction vessel at 30°-40°C. maintained with cooling. The molar ratio of formaldehyde:piperazine was 1.38:1. The reaction product slurry (containing 19 wt.% water in the solvent) was then hydrogenated by charging it to an autoclave containing a powdered nickel hydrogenation catalyst (Harshaw Ni-0104, supra) which was heated at 90°C. under a pressure of 50 psig of hydrogen. Hydrogenation was complete in 2 hours. GLC analysis of the product, on a solvent-free basis, was 43.6% 1,4-dimethylpiperazine, 55.7% 1-methylpiperazine, and no piperazine.

A comparison of the results of the above examples, particularly Examples VI–X, illustrate that at formaldehyde:piperazine molar ratios above 1.3, the employment of methanol as the solvent results in the formation of crude products of 1-methylpiperazine and 1,4-dimethylpiperazine free of piperazine impurities, while the employment of ethanol, isopropanol or water as the solvent, even with the employment of formaldehyde:piperazine ratios as high as 1.6:1, result in crude methylolated piperazine products still containing piperazine impurities.

EXAMPLE XI

To a solution of 1053 g. (13.0 moles) of 37% formalin was added 1940 g. (10.0 moles) of piperazine hexahydrate (44.3% piperazine, 55.7% water) in 2,000 g. of methanol. The piperazine-methanol solution was added over a period of 35 minutes with stirring at 50°-60°C. and stirring was then continued at 60°C. for 30 minutes longer. This slurry was then hydrogenated at 90°C. and 50 psig of hydrogen in the presence of 65 g. of a powdered nickel catalyst (Harshaw Ni-1404, Harshaw Chemical Company) for 3 hours in a 3-gallon autoclave. The amount of water present during hydrogenation was 48% wt.% of the total solvent. The product was analyzed by gas liquid chromatography and found to contain (area percent, solvent-free basis) 41.9% 1,4-dimethylpiperazine, 56.6% 1-methylpiperazine, and 1.2% piperazine. A comparison of the results of this example with those of Example VII, which employed the same molar ratio of formaldehyde:piperazine (1.3:1) illustrates the effect on piperazine content in the crude reaction product when excess water was present as a solvent.

EXAMPLE XII

A solution of 142 g. (0.93 mole) of piperazine-water eutectic (56.4% piperazine, 43.6% water, by weight) dissolved in 308 g. of methanol was added to 116 g. of 37% formalin (1.4 moles formaldehyde) previously charged to an appropriate reaction vessel equipped with stirring and cooling means. The temperature of the reaction mixture during addition was maintained at 30°-40°C. with cooling. The reaction product slurry, a 1.5:1 molar ratio of formaldehyde:piperazine, contained 32% water by weight in the water-methanol solvent. The slurry was then hydrogenated in an autoclave equipped for stirring containing 10 g. of a nickel-containing hydrogenation catalyst. Hydrogenation was carried out at 90°C. under 50 psig, maintained by intermittent hydrogen introduction, which required 3 hours for completion. The composition of the hydrogenation product, determined by gas liquid chromatography on a solvent-free basis, was 53.1% 1,4-dimethylpiperazine and 44.2% 1-methylpiperazine, with no piperazine detected.

EXAMPLE XIII

A solution of 194 g. (1.0 mole) of piperazine hexahydrate in 105 g. of methanol was added to 113 g. (1.4 mole) of 37% formalin during which the temperature was maintained at 40°–45°C. with cooling. This very thick slurry, containing 64% water by weight in the total solvent present, was charged to a stirred autoclave together with 8 g. of nickel hydrogenation catalyst (Harshaw Ni-0104, supra) and heated at 88°–95°C. under 50 psig in the presence of hydrogen, the pressure being maintained with intermittent hydrogen introduction. Hydrogenation under these conditions required more than 8 hours for completion, indicated by cessation of hydrogen consumption. The hydrogenation product was analyzed by gas liquid chromatography on a solvent-free basis and found to consist of 46.8% 1,4-dimethylpiperazine, 46.7% 1-methylpiperazine, 3.5% piperazine, and 2.8% higher boiling impurities. A comparison of the results of this example to the results of Example XII illustrates the criticality of utilizing methanol as the major solvent during hydrogenation of the formaldehyde-piperazine reaction product. The comparison also demonstrates the criticality of the amount of water present during the hydrogenation step of the formaldehyde-piperazine reaction product.

The following Table 1 sets forth the results of the above Examples I-XIII, along with the formaldehyde:piperazine molar ratios, major solvent, and amount of water present in the solvent in each example, for comparison to illustrate the critical features of the present invention.

genating the resulting reaction product in said liquid solvent in the presence of a hydrogenation catalyst at an elevated temperature in liquid phase, the improvement comprising the step of:

mixing and reacting the formaldehyde and piperazine in a molar ratio of from more than 1.3:1 to less than about 2.0:1;

hydrogenating the formaldehyde:piperazine reaction product using methanol as the major solvent of said liquid solvent, wherein the liquid solvent contains less than about 35% water by weight, based upon the total weight of the liquid solvent present, whereby the resulting crude hydrogenated product is essentially free from piperazine as an impurity; and recovering the 1-methylpiperazine and 1,4-dimethylpiperazine co-products.

2. The process of claim 1 wherein the methanol is mixed with said formaldehyde and piperazine in an amount sufficient to provide a viscosity of said formaldehyde:piperazine reaction product that permits stirring thereof.

3. The process of claim 2 wherein said methanol is added to said formaldehyde and piperazine in an amount sufficient to provide a resulting reaction product concentration of from about 15% to about 30% by weight, based upon the total weight of formaldehyde and piperazine reaction product and liquid solvent present.

4. The process of claim 1 wherein the liquid solvent used during the hydrogenation of the formaldehyde:piperazine reaction product contains less than about 30% water, based upon the total weight of liquid solvent present.

5. The process of claim 1 wherein the molar ratio of

Table 1

| Example | Formaldehyde:Piperazine Molar Ratio | Major Solvent Carrier | Water Present[1] wt. % in Solvent | NMP[3] | Products[2] DMP[4] | PIP[5] | Unknown[6] |
|---|---|---|---|---|---|---|---|
| I | 1.37:1 | Methanol | 14 | 58.0 | 41.7 | 0 | 0.3[7] |
| II | 1.03:1 | Methanol | 12 | 75.0 | 16.3 | 8.6 | |
| III | 1.22:1 | Methanol | 21 | 72.3 | 26.7 | 0.7 | |
| IV | 1.387:1 | Methanol | 19 | 55.2 | 42.0 | 0 | Trace |
| V | 1.4:1 | Water | 100 | 39.2 | 47.7 | 6.2 | 6.7 |
| VI | 1.4:1 | Water | 100 | 41.9 | 48.2 | 7.4 | 2.3 |
| VII | 1.3:1 | Methanol | 17 | 67.1 | 31.9 | 0.2 | |
| VIII | 1.6:1 | Ethanol | 25 | 38.2 | 60.4 | 0.5 | |
| IX | 1.6:1 | Isopropanol | 25 | 30.4 | 68.1 | 0.3 | |
| X | 1.38:1 | Methanol | 19 | 55.7 | 43.6 | 0 | |
| XI | 1.3:1[8] | Methanol | 48 | 56.6 | 41.9 | 1.2 | |
| XII | 1.5:1[9] | Methanol | 32 | 44.2 | 53.1 | 0 | |
| XIII | 1.4:1[10] | Methanol | 64 | 46.7 | 46.8 | 3.5 | 2.8 |

[1]wt. % water present was calculated on weight of total solvent in reaction product slurry before hydrogenation.
[2]Analysis by gas liquid chromatography, wt. % and solvent-free basis.
[3]1-methylpiperazine.
[4]1,4-dimethylpiperazine.
[5]piperazine
[6]minor higher boiling materials.
[7]N,N-dimethylaminoethanol, from monoethanol impurity.
[8]piperazine hexahydrate (44.3% piperazine, 55.7% water, by weight).
[9]piperazine-water eutectic (56.4% piperazine, 43.6 water, by weight).
[10]piperazine hexahydrate.

From the foregoing description and examples of this invention, those of ordinary skill in the art may make many modifications and variations therefrom without departing from the scope of the invention as hereinafter claimed.

We claim:

1. In a process for the preparation of 1-methylpiperazine and 1,4-dimethylpiperazine as co-products comprising mixing and reacting formaldehyde and piperazine in the presence of a liquid solvent and then hydroformaldehyde:piperazine is within the range of from more than 1.3:1 to about 1.7:1.

6. The process of claim 5 wherein methanol is added to said formaldehyde and piperazine in an amount sufficient to provide a resulting reaction product concentration of about 15 to about 30% by weight, based upon the total weight of formaldehyde-piperazine reaction product and solvent present.

7. The process of claim 6 wherein the liquid solvent employed during the hydrogenation of the formaldehyde:piperazine reaction product contains less than about 30% water, based upon the total weight of liquid solvent present.

8. The process in accordance with claim 1 wherein the formaldehyde:piperazine reaction product is hydrogenated in the methanol solvent, including less than 35 wt.% water present, by heating the reaction product-solvent mixture in the presence of hydrogen and a nickel or cobalt-containing hydrogenation catalyst at a temperature of between about 60°C. to about 130°C. under a pressure of from about atmospheric to about 4,000 psig.

9. A process for the preparation of 1-methylpiperazine and 1,4-dimethylpiperazine as co-products in essentially pure forms free from piperazine as an impurity, said process comprising the step of:

admixing an aqueous solution of formaldehyde, piperazine and methanol at a temperature of from about 30°C. to about 60°C., said formaldehyde aqueous solution, piperazine and methanol being admixed in amounts sufficient to provide a molar ratio of more than 1.3:1 to about 1.7:1 formaldehyde:piperazine, a resulting formaldehyde-piperazine reaction product slurry containing less than 35 wt.% water, based upon the total weight of methanol and water present in said resulting slurry and a formaldehyde-piperazine reaction product concentration of about 15% to about 30%, based upon the total weight of said slurry;

heating the reaction product slurry in the presence of hydrogen and a nickel or cobalt-containing hydrogenation catalyst at a temperature of from about 60°C. to about 130°C. under a pressure of from about atmospheric to about 4,000 psig;

maintaining said pressure by intermittent introduction of hydrogen until hydrogen consumption has ceased; and recovering 1-methylpiperazine and 1,4-dimethylpiperazine essentially free of piperazine as an impurity.

* * * * *